US006071957A

United States Patent [19]

Miller et al.

[11] Patent Number: 6,071,957

[45] Date of Patent: Jun. 6, 2000

[54] IRREVERSIBLE NON-STEROIDAL ANTAGONIST COMPOUND AND ITS USE IN THE TREATMENT OF PROSTATE CANCER

[75] Inventors: Duane D. Miller, Germantown; Leonid I. Kirkovsky, Memphis; James T. Dalton, Memphis; Arnab Mukherjee, Memphis, all of Tenn.

[73] Assignee: The University of Tennessee Research Corporation, Knoxville, Tenn.

[21] Appl. No.: 08/978,511

[22] Filed: Nov. 25, 1997

Related U.S. Application Data

[60] Provisional application No. 60/031,861, Nov. 27, 1996.

[51] Int. Cl.[7] ........................ A61K 31/275; C07C 255/50

[52] U.S. Cl. .......................... 514/522; 514/150; 514/508; 514/617; 514/618; 514/619; 514/620; 552/8; 558/13; 558/413; 564/162; 564/163; 564/164; 564/165; 564/155

[58] Field of Search .................................... 558/411, 412, 558/413, 414, 415, 17, 13; 514/519, 520, 524, 617, 618, 619, 620, 150, 508, 522; 564/162, 155, 163, 164, 165; 552/8

[56] References Cited

U.S. PATENT DOCUMENTS

| | | |
|---|---|---|
| 3,875,229 | 4/1975 | Gold . |
| 4,139,638 | 2/1979 | Neri et al. . |
| 4,191,775 | 3/1980 | Glen . |
| 4,239,776 | 12/1980 | Glen et al. . |
| 4,282,218 | 8/1981 | Glen et al. . |
| 4,386,080 | 5/1983 | Crossley et al. . |
| 4,636,505 | 1/1987 | Tucker . |
| 4,880,839 | 11/1989 | Tucker . |

FOREIGN PATENT DOCUMENTS

| | | |
|---|---|---|
| 0002892 A1 | 7/1979 | European Pat. Off. . |
| 0040932 | 12/1981 | European Pat. Off. . |
| 0100172 | 2/1984 | European Pat. Off. . |
| 52-128329 | 10/1977 | Japan . |
| 54-63047 | 5/1979 | Japan . |
| 1360001 | 7/1974 | United Kingdom . |
| 9519770 | 7/1995 | WIPO . |

OTHER PUBLICATIONS

Tucker et al, J. Med. Chem, vol. 31, pp. 885–887, 1988.

McKillop et al, Xenobiotica, vol. 25, No. 6, pp. 623–634, 1995.

Kirkovsky et al., "Approaches to Irreversible Non–Steroidal Chiral Antiandrogens,"47th Southeast/51st Southwest Joint Regional Meeting of the American Chemical Society, Memphis, TN (Nov. 29–Dec. 1, 1995).

*Primary Examiner*—Shailendra Kumar
*Attorney, Agent, or Firm*—Nixon Peabody LLP

[57] ABSTRACT

The present invention relates to an antiandrogen compound and a method of treating prostate cancer in a patient utilizing the compound. The present invention also relates to a pharmaceutical composition which includes the compound.

15 Claims, 3 Drawing Sheets

FIG. 1
CHEMICAL STRUCTURE AND AR BINDING AFFINITIES OF PRELIMINARY AFFINITY LABELS
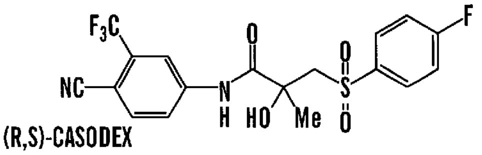
(R,S)-CASODEX
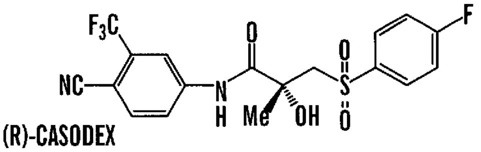
(R)-CASODEX
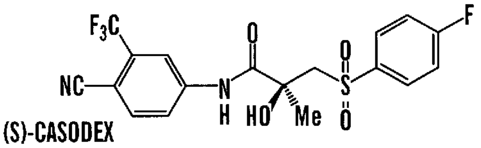
(S)-CASODEX
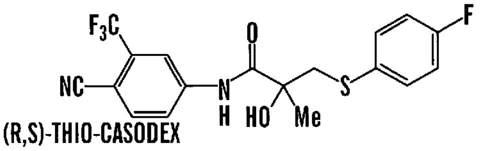
(R,S)-THIO-CASODEX
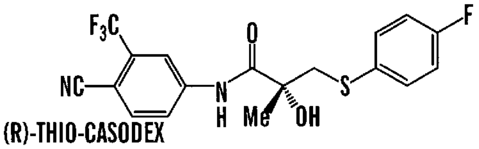
(R)-THIO-CASODEX
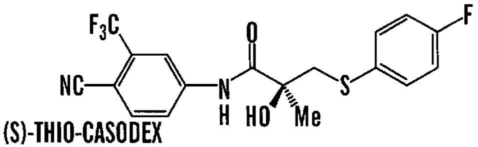
(S)-THIO-CASODEX
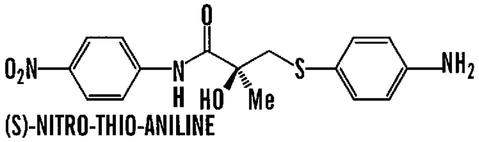
(S)-NITRO-THIO-ANILINE
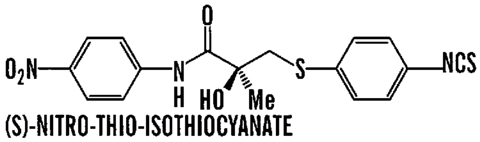
(S)-NITRO-THIO-ISOTHIOCYANATE
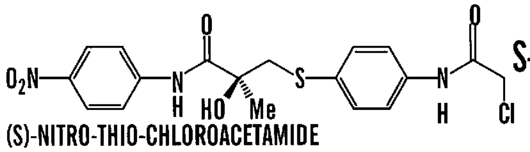
(S)-NITRO-THIO-CHLOROACETAMIDE
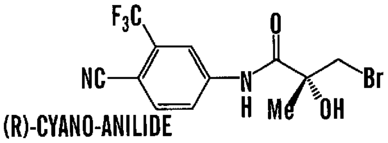
(R)-CYANO-ANILIDE
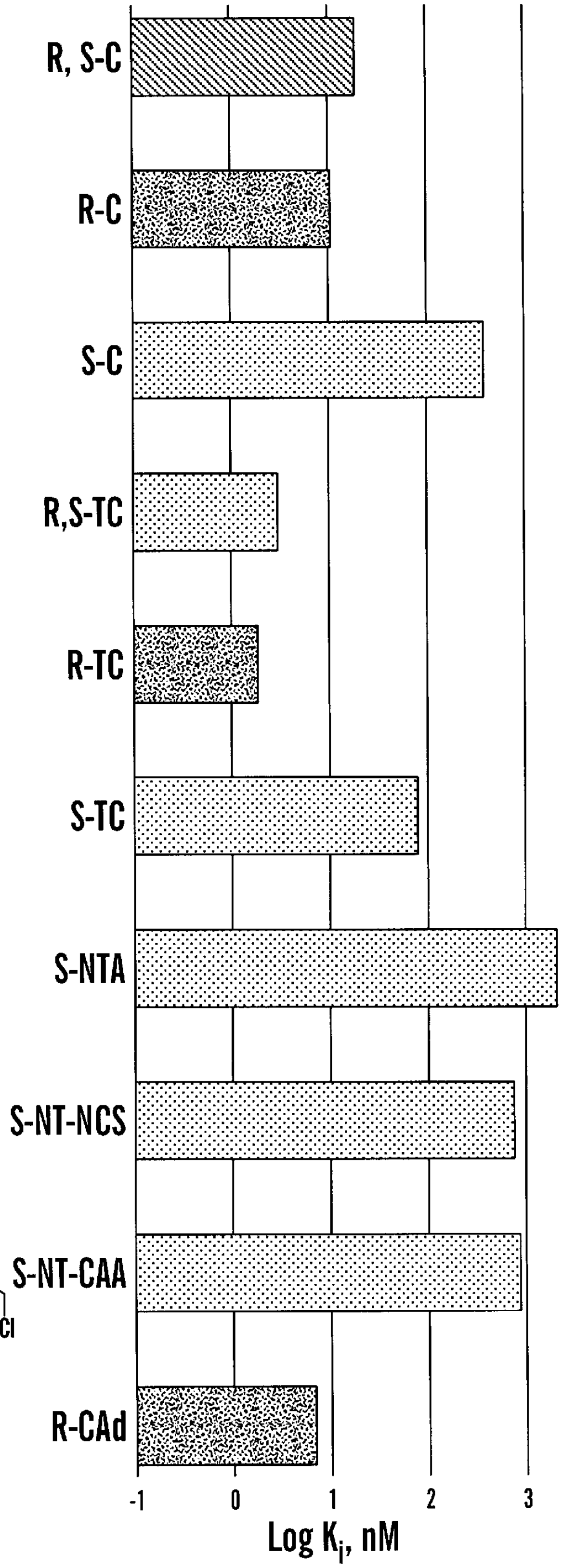

*FIG. 2*

BINDING AFFINITIES OF THE R-ISOMERS OF POTENTIAL IRREVERSIBLE COMPOUNDS

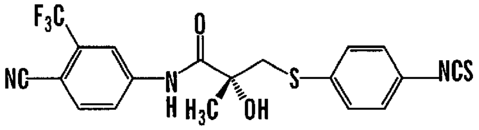

(R)-CYANOTRIFLUORO-THIO-p-ISOTHIOCYANATE

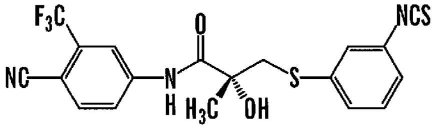

(R)-CYANOTRIFLUORO-THIO-m-ISOTHIOCYANATE

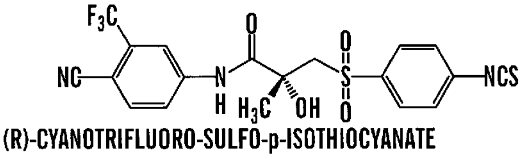

(R)-CYANOTRIFLUORO-SULFO-p-ISOTHIOCYANATE

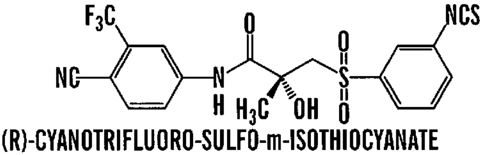

(R)-CYANOTRIFLUORO-SULFO-m-ISOTHIOCYANATE

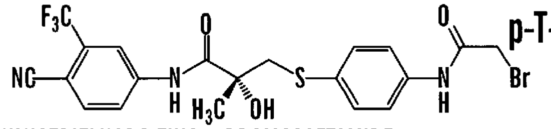

(R)-CYANOTRIFLUORO-THIO-p-BROMOACETAMIDE

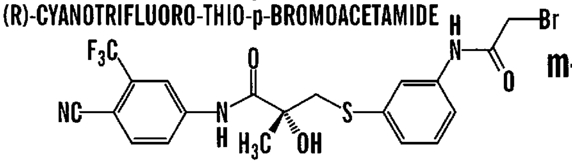

(R)-CYANOTRIFLUORO-THIO-m-BROMOACETAMIDE

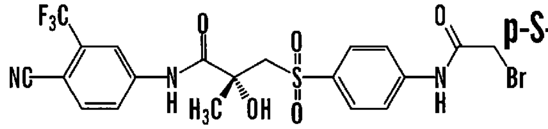

(R)-CYANOTRIFLUORO-SULFO-p-BROMOACETAMIDE

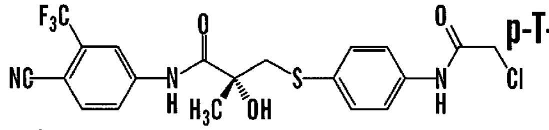

(R)-CYANOTRIFLUORO-THIO-p-CHLOROACETAMIDE

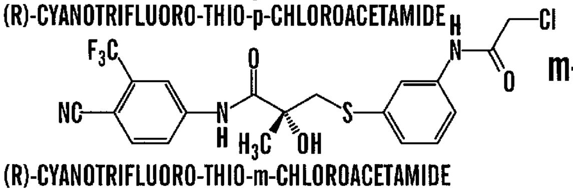

(R)-CYANOTRIFLUORO-THIO-m-CHLOROACETAMIDE

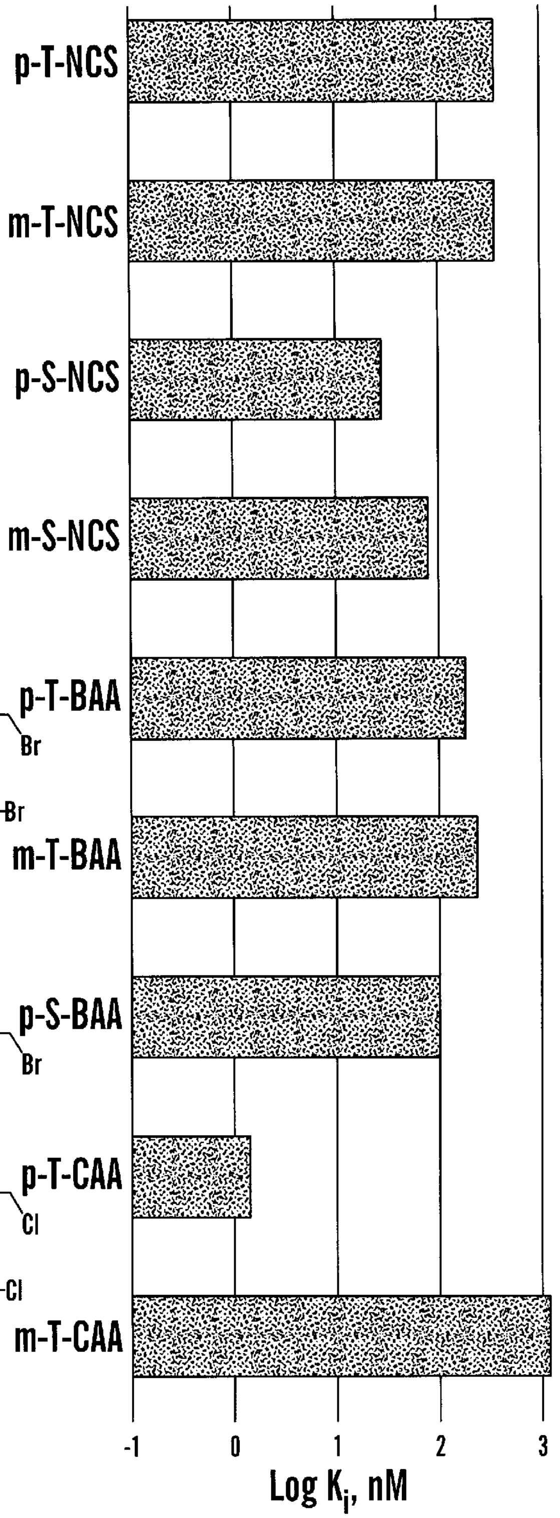

IRREVERSIBLE NON-STEROIDAL ANTAGONIST COMPOUND AND ITS USE IN THE TREATMENT OF PROSTATE CANCER

The present application claims the benefit of U.S. Provisional Patent Application Serial No. 60/031,861, filed Nov. 27, 1996.

FIELD OF THE INVENTION

The present invention relates to non-steroidal antagonist compounds and their use in treatment of prostate cancer. More particularly, the present invention relates to an irreversible non-steroidal antiandrogen and its use in treating prostate cancer.

BACKGROUND OF THE INVENTION

Prostate cancer is the most common cancer in men with an estimated 244,000 cases in 1995 in the United States. It is the second leading cause among men who die from neoplasia with an estimated 44,000 deaths per year. Prompt detection and treatment is needed to limit mortality caused by prostate cancer.

As described in W. J. Catalona, "Management of Cancer of the Prostate," New Engl. J. Med. 331(15):996–1004 (1994) (which is hereby incorporated by reference), the management of prostate cancer can be achieved by watchful waiting, curative treatment, and palliation. For men with a life expectancy of less than 10 years, watchful waiting is appropriate where low-grade, low-stage prostate cancer is discovered at the time of a partial prostatectomy for benign hyperplasia. Such cancers rarely progress during the first five years after detection. On the other hand, for younger men, curative treatment is often more appropriate.

Where prostate cancer is localized and the patient's life expectancy is 10 years or more, radical prostatectomy offers the best chance for eradication of the disease. Historically, the drawback of this procedure is that most cancers had spread beyond the bounds of the operation by the time they were detected. However, the use of prostate-specific antigen testing has permitted early detection of prostate cancer. As a result, surgery is less expensive with fewer complications. Patients with bulky, high-grade tumors are less likely to be successfully treated by radical prostatectomy.

After surgery, if there are detectable serum prostate-specific antigen concentrations, persistent cancer is indicated. In many cases, prostate-specific antigen concentrations can be reduced by radiation treatment. However, this concentration often increases again within two years.

Radiation therapy has also been widely used as an alternative to radical prostatectomy. Patients generally treated by radiation therapy are those who are older and less healthy and those with higher-grade, more clinically advanced tumors. Particularly preferred procedures are external-beam therapy which involves three dimensional, conformal radiation therapy where the field of radiation is designed to conform to the volume of tissue treated, and interstitial-radiation therapy where seeds of radioactive compounds are implanted using ultrasound guidance.

Cytotoxic chemotherapy is largely ineffective in treating prostate cancer. Its toxicity makes such therapy unsuitable for elderly patients. In addition, prostate cancer is relatively resistant to cytotoxic agents.

Androgens are known to stimulate growth of the prostate and other peripheral tissues, including primary or metastatic prostate tumor cells. Testosterone ("T") is the principal androgen secreted by the testes and is the primary circulating androgen found in the plasma of males. The testes produce 95% of circulating plasma T, while the remaining 5% is derived from the adrenals. In many target tissues, T is converted by the enzyme 5α-reductase to the more potent androgen dihydrotestosterone ("DHT"). T and DHT then compete for binding to the androgen receptor ("AR") to exert their influence on cell function. DHT has a four- to five-fold higher AR binding affinity than does T and thus serves as the intracellular mediator for most actions of the hormone. However, both androgens contribute to the overall androgenic effect. The high response rate (i.e., 60 to 80%) to first line hormonal therapy and the presence of AR in both primary and metastatic prostate tumor cells support the idea that the AR is an important mediator of prostate cancer development and growth. Denis et al., "Prostatic Cancer: An Overview," *Acta. Oncol.,* 29:665–677 (1990); McConnell, "Physiologic Basis of Endocrine Therapy for Prostatic Cancer," *Urol. Clin. N. Am.,* 18(1):1–13 (1991) (which are hereby incorporated by reference)

Because prostatic carcinomas are androgen dependent, various treatment strategies focus on negating the role of androgens (i.e., testosterone and dihydrotestosterone) in prostate tumor growth. Labrie, "Endocrine Therapy for Prostate Cancer," *Endocrinol. Metab. Clin. N. Am.,* 20(4) :845-872 (1991); Soloway, et al., "Antiandrogenic Agents as Monotherapy in Advanced Prostatic," *Cancer,* 71(Suppl. 3): 1083–1088 (1993) (which are hereby incorporated by reference). These treatment strategies include use of luteinizing hormone-releasing hormone ("LHRH") to suppress testicular androgen production or orchiectomy (surgical castration) to eliminate androgen production.

In recent years, antiandrogens have been widely used for the treatment of prostate cancer. The biologic activity of androgens is mediated through the formation of a non-covalent androgen receptor-steroid complex. Antiandrogens inhibit formation if this complex and, thus, negate the role of endogenous steroids in androgen-dependent growth of the prostate.

Antiandrogens can be divided into two groups: steroidal and non-steroidal. There are several non-steroidal antiandrogens such as Flutamide (Eulexin), Nilutamide (Anandrone), and Casodex. All of them bind reversibly to the AR. Accordingly, these antiandrogens can be displaced by an endogenous ligand such as dihydrotestosterone. Therefore, these antiandrogens have not been successful in the treatment of prostate cancer. Earlier reports suggested that dihydrotestosterone bromoacetate (DHT-BA) binds irreversibly to the AR. However, recent evidence showed that DHT-BA binds aldehyde dehydrogenase, and not the AR. McCammon et al., "An Androgenic Affinity Ligand Covalently Binds to Cytosolic Aldehyde Dehydrogenase from Human Genital Skin Fibroplast," *Mol. Cell. Endocrinology,* 91:177–183 (1993), which is hereby incorporated by reference. Therefore, DHT-BA is not suitable for treating prostate cancer.

The present invention is directed to overcoming these deficiencies.

SUMMARY OF THE INVENTION

The present invention relates to a method of treating prostate cancer in a patient which includes administering to the patient an effective amount of a compound which binds irreversibly to the androgen receptor of the patient.

Another aspect of the present invention relates to a method of treating prostate cancer in a patient which includes administering to the patient an effective amount of a compound having the formula:

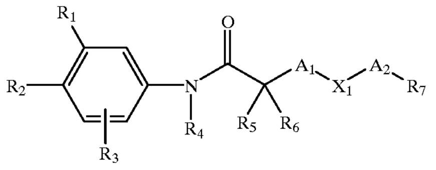

where $R_1$, $R_2$ and $R_3$, are the same or different and are a hydrogen, a nitro, a cyano, a carbamoyl, a halogen, a perfluoroalkyl, a haloalkylamido, an isothiocyanate, an azide, a diazocarbonyl, a substituted oxirane, or a β-chloroethylamine $R_4$ is a hydrogen, an alkyl, or is joined to $R_5$;

$R_5$ is a hydrogen, a hydroxy, an alkoxy, an acyloxy, an amino, an alkylamino, a halogen, or is joined to $R_4$;

$R_6$ is a hydrogen, an alkyl, or a halogenoalkyl;

$A_1$ and $A_2$ are the same or different, and each is a direct link or an alkylene;

$X_1$ is a halogen, an oxygen, a sulfur, a sulphinyl, a sulphonyl, an amino, or an alkylimino, or alkylene;

$R_7$ is a hydrogen, a halogen, an alkoxy, a haloalkoxy, an acyloxy, a haloacyloxy, an aryloxy, a thioalkyl, a thioraryl, a sulphinyl, a haloalkyl sulphinyl, a sulphonyl, a haloalkylsulphonyl, an amino, an alkylimino, an alkylamido group, a haloalkylamido group, an isothiocyanate, an azide, a diazocarbonyl, a substituted oxirane, a β-chloroethylamine, or a phenyl optionally substituted with halogen, a nitro group, an alkyl, a haloalkyl, a cyano, a hydroxyl, a carboxylic group, an amino, an alkylamino, an alkylamido group, a haloalkylamido group, an isothiocyanate, an azide, a diazocarbonyl, a substituted oxirane, or a β-chloroethylamine. The compound binds irreversibly to an androgen receptor of the patient.

The present invention also relates to the compound and to a pharmaceutical composition which includes the compound and a pharmaceutically suitable carrier.

BRIEF DESCRIPTION OF THE DRAWINGS

FIG. 1 shows the chemical structure and AR binding affinities of compounds of the present invention.

FIG. 2 shows the binding affinities of compounds of the present invention.

DETAILED DESCRIPTION OF THE INVENTION

Figure 3:
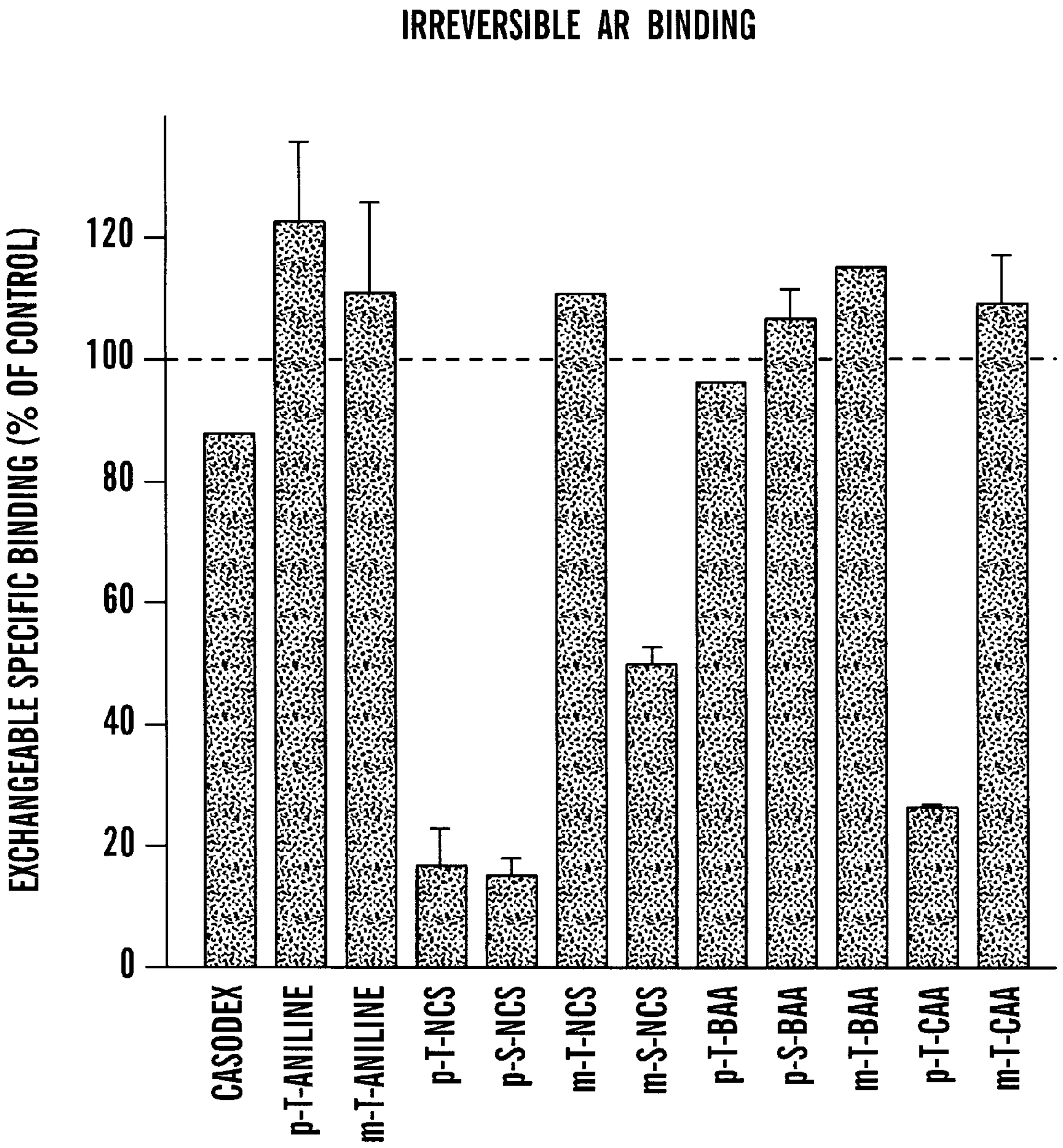
FIG. 3 shows the irreversible binding of compounds of the present invention to AR.

The present invention relates to a method of treating prostate cancer in a patient which includes administering to the patient an effective amount of a compound which binds irreversibly to the androgen receptor of the patient.

The present invention relates to a method of treating prostate cancer in a patient which includes administering to the patient an effective amount of a compound having the formula:

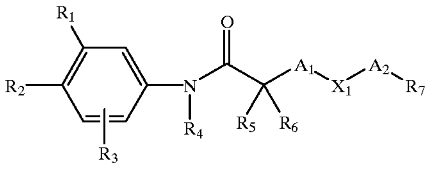

where $R_1$, $R_2$, and $R_3$ are the same or different and are a hydrogen, a nitro, a cyano, a carbamoyl, a halogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a hydrogen, a hydroxy, an alkoxy, an acyloxy, an amino, an alkylamino, a halogen, or is joined to $R_4$;

$R_6$ is a hydrogen, an alkyl, or a halogenoalkyl;

$A_1$ and $A_2$ is the same or different, each is direct link or an alkylene;

$X_1$ is a halogen, an oxygen, a sulfur, a sulphinyl, a sulphonyl, an amino, an alkylimino, or an alkylene;

$R_7$ is a hydrogen, a halogen, an alkoxy, a haloalkoxy, a acyloxy, a haloacyloxy, an aryloxy, a thioalkyl, a thioraryl, a sulphinyl, a haloalkyl sulphinyl, a sulphonyl, a haloalkylsulphonyl, an amino, an alkylimino, an alkylamido group, a haloalkylamido group, an isothiocyanate, an azide, a diazocarbonyl, a substituted oxirane, a β-chloroethylamine, or a phenyl optionally substituted with a halogen, a nitro group, an alkyl, a haloalkyl, a cyano, a hydroxyl, a carboxylic group, an amino, an alkylamino, an alkylamido group, a haloalkylamido group, an isothiocyanate, an azide, a diazocarbonyl, a substituted oxirane, or a β-chloroethylamine. The compound binds irreversibly to an androgen receptor of the patient.

The subject invention is best understood through a discussion of receptors and signal transduction pathways. Cells in higher animals normally communicate by means of hundreds of kinds of extracellular signaling molecules, including proteins, small peptides, amino acids, nucleotides, steroids, retinoids, fatty acid derivatives, and even dissolved gases such as nitric oxide and carbon monoxide. These signaling molecules relay a "signal" to another cell (a "target cell"), generally affecting a cellular function. As used herein, receptors for extracellular signaling molecules are collectively referred to as "cell signaling receptors".

Many cell signaling receptors are transmembrane proteins on a cell surface; when they bind an extracellular signaling molecule (a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor must have certain attributes, other than affinity, in order to activate the cell. Chemical bonds between atoms of the substance and the atoms of the receptors must form. In some cases, this leads to a slight change in the configuration of the receptor which is enough to begin the activation process (called signal transduction). As a result, substances can be made which bind receptors and activate them (called receptor agonists) or inactivate them (called receptor antagonists).

The present invention is directed to compounds which are antagonists compounds, and are, therefore, useful in blocking steroidal hormone receptors. Preferably, the antagonist compound of the present invention is an antiandrogen which binds the androgen receptor. More particularly, the present invention is a compound which binds irreversibly to the androgen receptor to inhibit formation of a androgen receptor-steroid complex to prevent prostate cancer. In particular, the compound of the present invention contains an active (i.e. electrophilic) functional group (or affinity label) that allows alkylation of the androgen receptor (i.e. allows covalent bond formation between the receptor and the functional group). Thus, the compound binds irreversibly to the receptor and, accordingly, cannot be displaced by the steroid, because of the chemical strength of the covalent interaction, the receptor is rendered permanently nonfunctional. In particular, the compound of the present invention irreversibly binds to the androgen receptor preventing displacement of the compound by the endrogenous ligands dihydrotestosterone and testosterone.

The compounds which are useful in binding irreversibly to the androgen receptor are acylanilides have the formula:

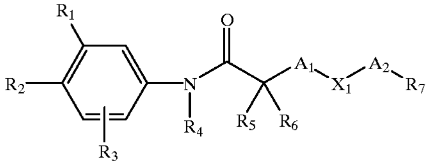

wherein $R_1$, $R_2$, and $R_3$ are the same or different,and each is a hydrogen, a nitro, a cyano, a carbamoyl, a halogen, a perfluoroalkyl, a haloalkylamido, an isothiocyanate, an azide, a diazocarbonyl, a substituted oxirane, a β-chloroethylamine, or other defined and exemplified substituents;

$R_4$ is a hydrogen, an alkyl, or is joined to $R_5$;

$R_5$ is a hydrogen, a hydroxy, an alkoxy, an acyloxyhalogen, o, an alkylamino, a halogen, or is joined to $R_4$;

$R_6$ is a hydrogen, an alkyl, or a halogenoalkyl;

$A_1$ and $A_2$ is the same or different, each is direct link or alkylene;

$X_1$ is a halogen, an oxygen, a sulfur, a sulphinyl, a sulphonyl, an amino, an alkylimino, or an alkylene; and $R_7$ is a hydrogen, a halogen, an alkoxy, a haloalkoxy, an acyloxy, a haloacyloxy, an aryloxy, a thioalkyl, a thioraryl, a sulphinyl, a haloalkyl sulphinyl, a sulphonyl, a haloalkylsulphonyl, an amino, an alkylimino, an alkylamido group, a haloalkylamido group, an isothiocyanate, an azide, a diazocarbonyl, a substituted oxirane, a β-chloroethylamine, or a phenyl optionally substituted with a halogen, a nitro group, an alkyl, a haloalkyl, a cyano, a hydroxyl, a carboxylic group, an amino, an alkylamino, an alkylamido group, a haloalkylamido group, an isothiocyanate, an azide, a diazocarbonyl, a substituted oxirane, a β-chloroethylamine, or other defined and exemplified substituents.

Although the compounds of the present invention have affinity labels at either the $R_7$ or $R_2$ position, compounds having the affinity label at other positions may be utilized.

In particular, the compounds shown below in Table 1 are useful in a method of treating prostate cancer in a patient where the compound binds irreversibly to the androgen receptor of the patient.

TABLE 1

| Compound | R-isomers Compound No. | S-isomers Compound No. |
|---|---|---|
| 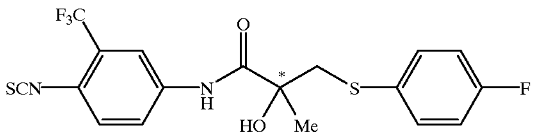 | R-1 | S-1 |
| 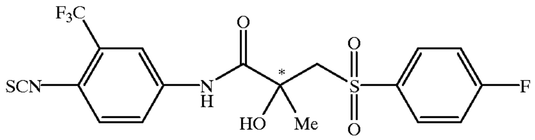 | R-2 | S-2 |

TABLE 1-continued
| Compound | R-isomers Compound No. | S-isomers Compound No. |
| --- | --- | --- |
| 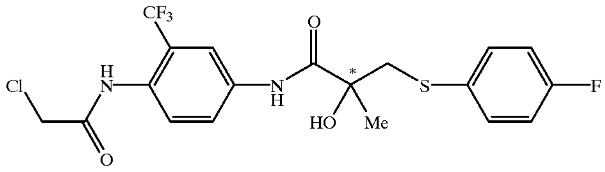 | R-3 | S-3 |
| 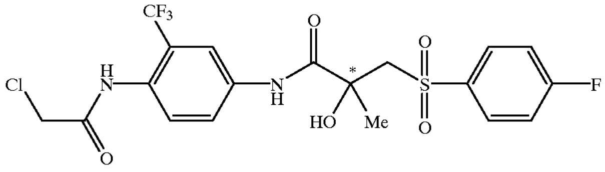 | R-4 | S-4 |
| 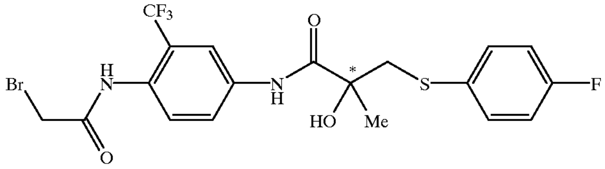 | R-5 | S-5 |
| 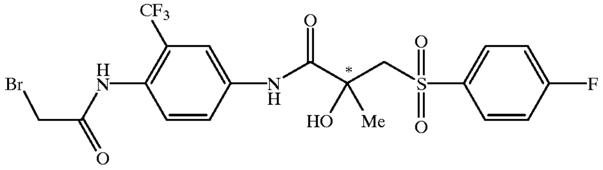 | R-6 | S-6 |
| 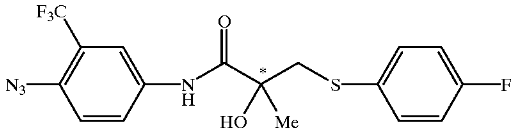 | R-7 | S-7 |
| 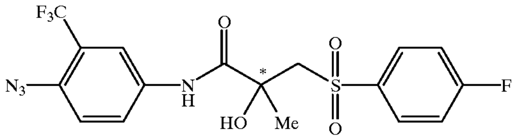 | R-8 | S-8 |
| 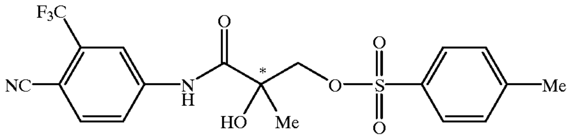 | R-9 | S-9 |
| 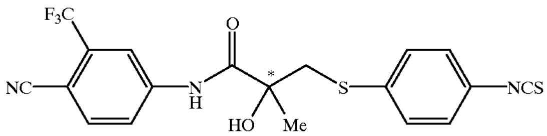 | R-10 | S-10 |
| 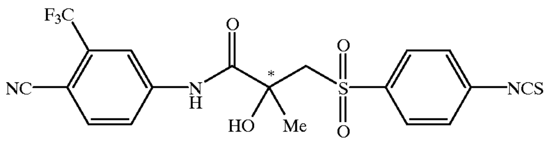 | R-11 | S-11 |

TABLE 1-continued
| Compound | R-isomers Compound No. | S-isomers Compound No. |
|---|---|---|
| 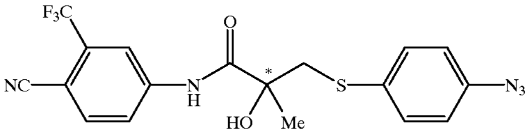 | R-12 | S-12 |
| 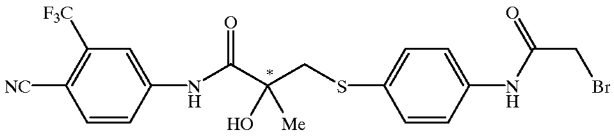 | R-13 | S-13 |
| 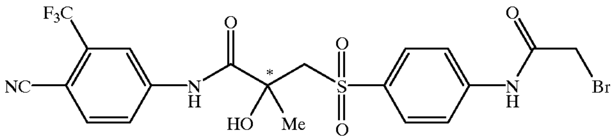 | R-14 | S-14 |
| 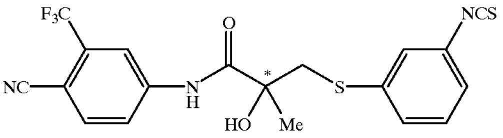 | R-15 | S-15 |
| 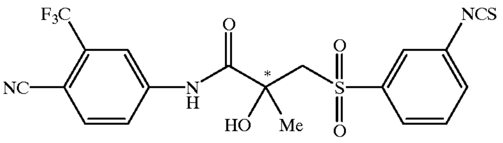 | R-16 | S-16 |
| 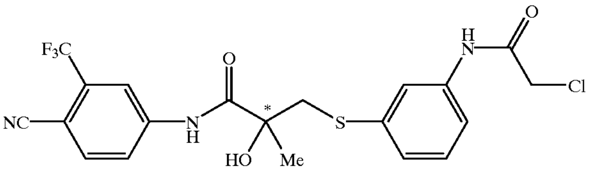 | R-17 | S-17 |
| 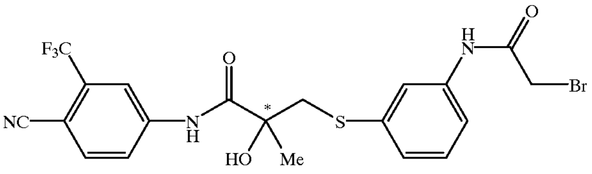 | R-18 | S-18 |
| 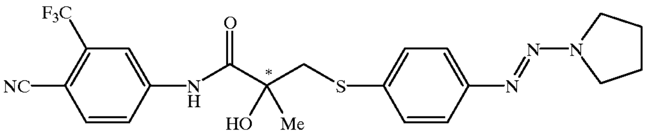 | R-19 | S-19 |
| 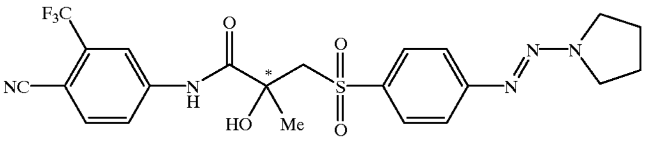 | R-20 | S-20 |
where Me is a methyl group.
Especially desirable compounds useful as antagonist compounds for treating prostate cancer have the formula:

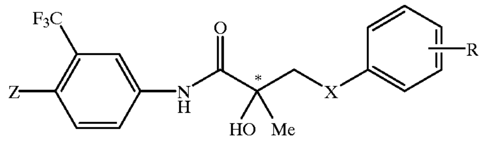

Where Z is NCS or CN, R is F, $NH_2$, NCS, $N_3$, or $NHCOCH_2Y$, X is S or $SO_2$, and Y is a halogen, preferably Cl or Br.

Particularly desirable compounds of the invention are where Z is CN, X is S, and R is either NCS or $NHCOCH_2$, Cl, or where Z is CN, X is $SO_2$, and R is NCS, or where Z is NCS, X is $SO_2$, and R is F.

As discussed above, the high response rate to first line hormonal therapy and the presence of AR in both primary and metastatic prostate tumor cells support the idea that AR is an important mediator of prostate cancer development and growth. Accordingly, by irreversibly binding the compound of the present invention to the AR of a patient, thereby blocking formation of the AR-hormone complex, the growth and development of prostate cancer is slowed or eliminated. The present invention, therefore, is directed to a method of treating prostate cancer in a patient where the compound of the present invention is administered to the patient in an effective amount, where the compound binds irreversibly to the androgen receptor of the patient.

The compounds herein may be made up in any suitable form appropriate for the desired use; e.g., oral, parenteral (for example, subcutaneously, intravenously, interamuscularly, intraperitoneally, by intranasal instillation, or by application to mucous membranes, such as that of the nose, throat, and bronchial tubes, or by instillation into hollow organ walls or newly vascularized blood vessels) or topical administration. Suitable dosage forms for oral use include tablets, dispersible powders, granules, capsules, suspensions, syrups, and elixirs. The compounds may be administered alone or with suitable pharmaceutical diluents or carriers. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

It will be appreciated that the actual preferred amount of the compound to be administered according to the present invention will vary according to the particular compound, the particular composition formulated, and the mode of administration. Many factors that may modify the action of the inhibitor can be taken into account by those skilled in the art; e.g., body weight, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

The acylanilides of the invention may be manufactured by any chemical process known to be suitable for the manufacture of chemically-analogous compounds. Examples of suitable chemical processes for manufacturing acylanilides are shown in U.S. Pat. No. 4,636,505 to Tucker, which is hereby incorporated by reference. One preferred process for the manufacture of an acylanilide of the invention comprises the reaction of an amine of the formula:

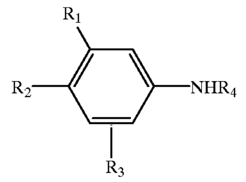

wherein $R_1$, $R_2$, $R_3$, are the same or different, and each is a hydrogen, a nitro, a cyano, a carbamoyl, a halogen, a perfluoroalkyl, a haloalkylamido, an isothiocyanate, an azide, a diazocarbonyl, a substituted oxirane, a β-chloroethylamine, or other defined and exemplifies substituents and $R_4$ is a hydrogen, or an alkyl, with an acid of the formula:

$$HO_2C—CR_5R_6—A_1\text{-}X_1—A_2—R_7$$

wherein $R_5$ is a hydrogen, a hydroxy, an alkoxy, an acyloxy, an amino, an alkylamino, a halogen; $R_6$ is a hydrogen, an alkyl, or a halogenoalkyl; $A_1$ and $A_2$ is the same or different, each is direct link or alkylene; $X_1$ is a halogen, an oxygen, a sulfur, a sulphinyl, a sulphonyl, an amino, an alkylimino, or an alkylene; and $R_7$ is a hydrogen, a halogen, an alkoxy, a haloalkoxy, an acyloxy, a haloacyloxy, an aryloxy, a thioalkyl, a thioraryl, a sulphinyl, a haloalkyl sulphinyl, a sulphonyl, a haloalkylsulphonyl, an amino, an alkylimino, an alkylamido group, a haloalkylamido group, an isothiocyanate, an azide, a diazocarbonyl, a substituted oxirane, a β-chloroethylamine, or a phenyl optionally substituted with a halogen, a nitro group, an alkyl, a haloalkyl, a cyano, a hydroxyl, a carboxylic group, an amino, an alkylamino, an alkylamido group, a haloalkylamido group, an isothiocyanate, an azide, a diazocarbonyl, a substituted oxirane, a β-chloroethylamine, or with a reactive derivative of said acid.

A suitable reactive derivative of an acid is, for example, an acid anhydride, or an acyl halide, for example an acyl chloride, or a lower alkyl ester of said acid, for example the methyl or ethyl ester. Preferably the reaction is carried out in N,N-dimethylacetamide solution using an acyl chloride (prepared from the acid and thionyl chloride) as reactant.

A second preferred process for the manufacture of an acylanilide of the invention wherein $R_5$ is hydroxy and $X_1$ is sulphur or alkylimino comprises the reaction of an epoxide of the formula:

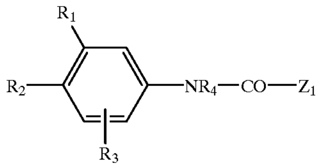

wherein $R_1$, $R_2$, $R_3$ and $R_4$ have the meanings stated above and wherein $Z_1$ has the formula:

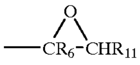 or $—CR_6OH—CHR_{11}Z_2$ wherein $R_6$ has the meaning stated above, wherein $Z_2$ is a displaceable group and wherein $R_{11}$ is such that $—CHR_{11}—$ is $—A_1$ as stated above, with a thiol or amine of the formula:

$R_7—A_2—SH$ or $R_7—A_2—NHR_{10}$ wherein $R_7$ and $A_2$ have the meanings stated above and $R_{10}$ is an alkyl.

A suitable value for $Z_2$ is, for example, a halogeno or sulphonyloxy group, for example the chloro, bromo, iodo, methanesulphonyloxy, or p-toluenesulphonyloxy group. The above-mentioned reaction is preferably carried out in an inert diluent or solvent, for example tetrahydrofuran, and in the presence of a base, for example sodium hydride.

The epoxide used as starting material may be obtained by the epoxidation, for example with a per-acid, of the corresponding unsaturated acylanilide.

A third preferred process for the manufacture of an acylanilide of the invention wherein $R_5$ is hydroxy comprises the reaction of a compound of the formula:

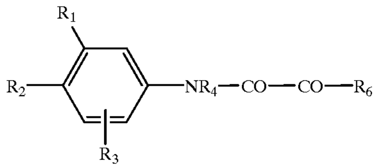

wherein $R_1$, $R_2$, $R_3$ and $R_4$ and $R_6$ have the meanings stated above, with an organometallic compound of the formula:

$R_7—A_2—X_1—A_1—M$ wherein $A_1$, $A_2$, $R_7$, and $X_1$ have the meanings stated above and M is a metal radical, for example the lithium radical.

The last-mentioned reaction is preferably carried out in an inert solvent, for example diethyl ether or tetrahydrofuran, at a low temperature, for example at between −60° C. and −100° C.

An acylanilide of the invention wherein $R_4$ and $R_5$ are joined together to form a carbonyloxy group, that is, an oxazolidinedione, may be prepared by the reaction of an isocyanate of the formula:

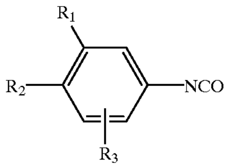

wherein $R_1$, $R_2$, and $R_3$ have the meanings stated above, with an ester of the formula:

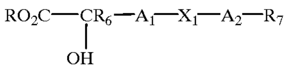

wherein $R_6$, $R_7$, $X_1$, $A_1$ and $A_2$ have the meanings stated above, and wherein R is alkyl of up to 6 carbon atoms, for example methyl or ethyl. This reaction is preferably carried out in an organic solvent, for example diethyl ether, at laboratory temperature.

An acylanilide of the invention wherein $R_5$ is hydroxy may be prepared by the hydrolysis of the corresponding acylanilide wherein $R_5$ is acyloxy, and an acylanilide of the invention wherein $R_5$ is hydroxy and $R_4$ is hydrogen may be prepared by the hydrolysis of the corresponding oxazolidinedione, which may be prepared as described in the preceding paragraph.

An acylanilide of the invention wherein $R_4$ is alkyl may be prepared by the alkylation of the corresponding acylanilide wherein $R_4$ is hydrogen.

An acylanilide of the invention wherein $R_5$ is acyloxy may be prepared by the acylation of the corresponding acylanilide wherein $R_5$ is hydroxy.

An oxazolidinedione of the invention, wherein $R_4$ and $R_5$ are joined together to form a carbonyloxy group, may be prepared by the reaction of the corresponding acylanilide wherein $R_4$ is hydrogen and $R_5$ is hydroxy with phosgene ($COCl_2$).

An acylanilide of the invention wherein $X_1$ or $X_2$ is sulphinyl or sulphonyl or wherein one or more of $R_1$, $R_2$, and a substituent in the phenyl or heterocyclic group $R_7$ is alkylsulphinyl, perfluoroalkylsulphinyl or phenylsulphinyl, or is alkylsulphonyl, perfluoroalkylsulphonyl or phenylsulphonyl, may be prepared by the oxidation of the corresponding acylanilide wherein $X_1$ or $X_2$ is sulphur or wherein one or more of $R_1$, $R_2$ and a substituent in the phenyl or heterocyclic group $R_7$, is alkylthio, perfluoroalkylthio or phenylthio. The oxidizing agent and conditions used will determine whether a sulphinyl or a sulphonyl compound is obtained. Thus, oxidation with sodium metaperiodate in methanol solution at or below laboratory temperature will generally convert a thiocompound into the corresponding sulphinyl compound; and oxidation with a per-acid, for example m-chloroperbenzoic acid, in methylene chloride solution at or above laboratory temperature will generally convert a thio compound into the corresponding sulphonyl compound.

A racemic acylanilide of the invention wherein $R_5$ is hydroxy may be separated into its optical isomers by forming an ester of the hydroxy group $R_5$ with an optically-active acid, for example (—)-camphanic acid, separating the diastereoisomeric esters thus obtained, by fractional crystallisation or, preferably, by flash-chromatography, and then hydrolyzing each separate ester to the alcohol. Alternatively, an optically active acylanilide of the invention may be obtained by using any of the processes described above with an optically active starting material.

As stated above, an acylanilide of the invention possesses antiandrogenic properties. An acylanilide of the invention may, therefore, be used in the treatment of malignant or benign prostatic disease or of other androgen dependent disease conditions, such as acne, hirsutism or seborrhoea, in a patient, such as warm-blooded vertebrates, including man. It may also be used to improve ovulation in a domestic animal. In addition, the compounds may be radiolabeled. Such radiolabeled ligands are useful for the detection of prostate cancer by the imaging and staging of localized and metastatic prostate tumors.

In another aspect of the present invention, compounds which are agonists to the androgen receptor bind to and activate the androgen receptor. Acylanides having the formula:

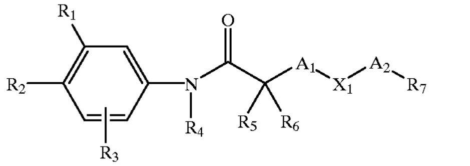

wherein $R_1$, $R_2$ and $R_3$, are the same or different and are a hydrogen, a nitro, a cyano, a carbamoyl, a halogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a hydrogen, a hydroxy, an alkoxy, an acyloxy, an amino, an alkylamino, a halogen, or is joined to $R_4$;

$R_6$ is a hydrogen, an alkyl, or a halogenoalkyl;

$A_1$ and $A_2$ is the same or different, each is direct link or alkylene;

$X_1$ is a halogen, an oxygen, a sulfur, a sulphinyl, a sulphonyl, an amino, an alkylimino, or an alkylene; and $R_7$ is a hydrogen, a halogen, an alkoxy, a haloalkoxy, an acyloxy, a haloacyloxy, an aryloxy, a thioalkyl, a thiorary, a sulphinyl, a haloalkyl sulphinyl, a sulphonyl, a haloalkylsulphonyl, an amino, an alkylimino, an alkylamido group, a haloalkylamido group, an isothiocyanate, an azide, a diazocarbonyl, a substituted oxirane, a β-chloroethylamine, or a phenyl optionally substituted with a halogen, a nitro group, an alkyl, a haloalkyl, a cyano, a hydroxyl, a carboxylic group, an amino, an alkylamino, an alkylamido group, a haloalkylamido group, an isothiocyanate, an azide, a diazocarbonyl, a substituted oxirane, or a β-chloroethylamine are useful as agonists of the androgen receptor and are, therefore, useful for a variety of therapeutic situations including male contraception and hormone replacement therapy. Compounds shown below in Table 2 are especially desirable agonists of the androgen receptor.

TABLE 2

| Compound | R-isomers Compound No. | S-isomers Compound No. |
|---|---|---|
| 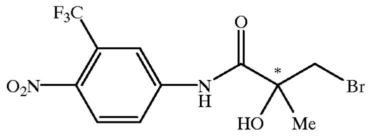 | R-1 | S-1 |
| 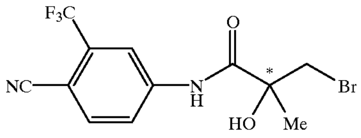 | R-2 | S-2 |
| 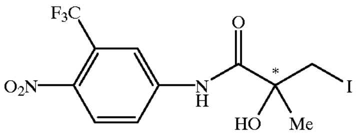 | R-3 | S-3 |
| 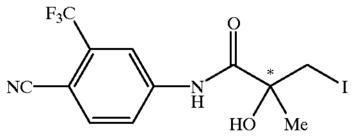 | R-4 | S-4 |
| 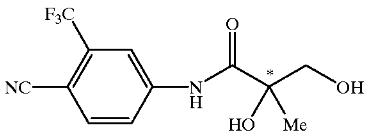 | R-5 | S-5 |

TABLE 2-continued

| Compound | R-isomers Compound No. | S-isomers Compound No. |
|---|---|---|
| 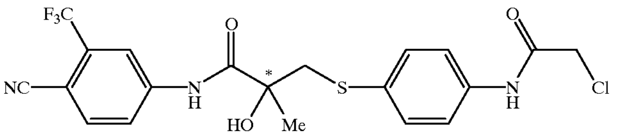 | R-6 | S-6 |

EXAMPLES

Example 1

(R)-and (S)-enantiomeric analogs of Casodex bearing affinity labels such as isothiocyanates, chloroacetamides, bromoacetamides, or azides were synthesized. The synthesized compounds according to the formula:

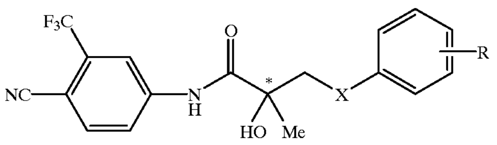

are shown in Table 3 below:

TABLE 3

| Substituents | | R-isomers | | S-isomer | |
|---|---|---|---|---|---|
| R | X | No. | $K_i$, nM | No. | $K_i$, nM |
| 4-$NH_2$ | S | R-1 | 70 | S-1 | 830 |
| 3-$NH_2$ | S | R-2 | 40 | S-2 | 2300 |
| 4-NCS | S | R-3 | 400 | S-3 | ≈4000 |
| 4-NCS | $SO_2$ | R-4 | 30 | | |
| 4-$N_3$ | S | R-5 | 11.5 | | |
| 4-$NHCOCH_2Cl$ | S | R-6 | 1.6 | | |

TABLE 3-continued

| Substituents | | R-isomers | | S-isomer | |
|---|---|---|---|---|---|
| R | X | No. | $K_i$, nM | No. | $K_i$, nM |
| 4-$NHCOCH_2Br$ | S | R-7 | 200 | | |
| 4-$NHCOCH_2Br$ | $SO_2$ | R-8 | 100 | | |
| 3-NCS | S | R-9 | 380 | S-9 | 2700 |
| 3-NCS | $SO_2$ | R-10 | 90 | | |
| 3-$NHCOCH_2Cl$ | S | R-11 | 1100 | | |
| 3-$NHCOCH_2Br$ | S | R-12 | 250 | | |

Analogs bearing an amine affinity labels were produced by the following procedure. (S)- or (R)-proline was used as the chiral matrix for syntheses of (R)- and (S)-anilines (R-1, R-2, S-1, and S-2 in Table 3) in Scheme 1 (shown below) as the starting materials for preparation of the affinity labels. This scheme is similar to the general synthetic route reported by Tucker and Chesterson for (S)-Casodex, in Tucker et al., "Resolution of the Non-steroidal Antiandrogen 4'-Cyano-3-[(4-flurophenyl)sulfonyl)]-2-hydroxy-2-methyl-3'-(trifluromethyl)-propioanilide and Determination of the Absolute Configuration of the Active Enantiomer," *J. Med. Chem.,* 31:885–887 (1988); Tucker et al., "Nonsteroidal Antiandrogens. Synthesis and Structure-Activity Relationships of 3-Substituted Derivatives of 2-Hydroxypropionanilides," *J. Med. Chem.,* 31(5)954–959 (1988).

Scheme 1

Synthesis of Amino Analogs of Casodex (with (S)-isomer as an example)

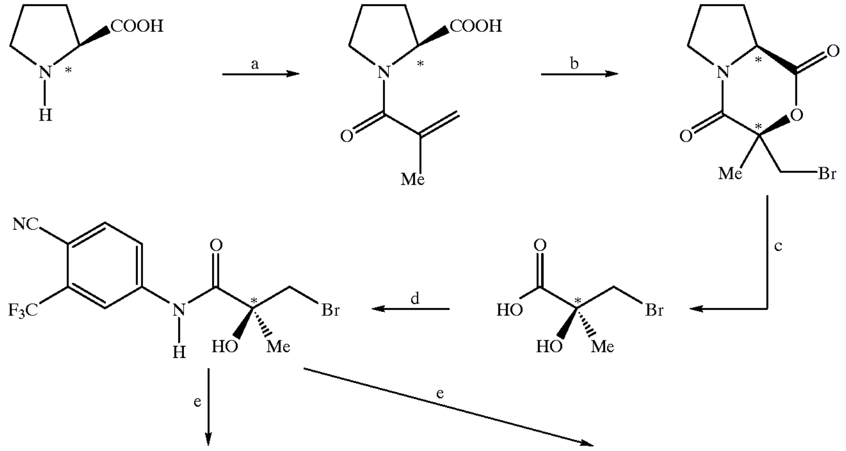

-continued

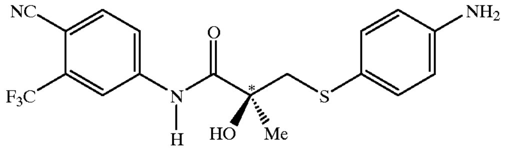

S-1

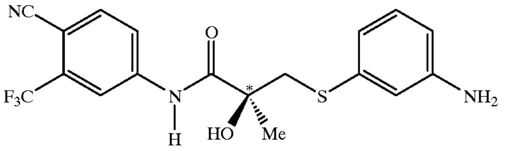

S-2

Analogs bearing an isothiocyanate affinity label were produced by the procedure shown in Scheme 2. Synthesis of the isothiocyanates (R-3 and R-9) was carried out with excellent yields (87–99%) according to the procedure of Leclerc et al., "Agens Alpha-adrenérgiques Alcoylants," 2, *Eur. J. Med. Chem.,* 18(4) 379–383 (1983), (shown in Scheme 2) in a two-phase aqueous-$CH_2Cl_2$-system. The thioester isothiocyanates (R-3 and R-9) were oxidized to the corresponding sulfone analogs (R- 4 and R-10) with good yields (55–60%) using m-chloroperbenzoic acid in $CH_2Cl_2$-solution according to Tucker et al., "Nonsteroidal Antiandrogens. Synthesis and Structure-Activity Relationships of 3-Substituted Derivatives of 2-Hydroxypropionanilides," *J. Med. Chem.,* 31(5)954–959 (1988).

Azide R-5 was synthesized through diazotization of the corresponding aniline R-1 followed by displacement of the diazonium salt with sodium azide. The yield of the reaction was 77%.

Chloroacetamides (R-6 and R-11) (yield 75–80%) and bromoacetamides (R-7 and R-12) (yield about 95%) (Scheme 3) were obtained according to Tindall's procedure for synthesis of DHT-BA, described Chang et al., "Affinity Labeling of the Androgen Receptor in the Rat Prostate Cytosol with 17β-[(Bromoacetyl)oxy]-5α-androstan-3-one, *Biochemistry,* 23:2527–2533 (1984). The use of sterically hindered N,N-diisopropylethylamine instead of triethylamine as the base avoided the undesirable reaction of bromoacetamide with the amine and gave excellent yields for these reactions. Oxidation of R-7 by m-chloroperbenzoic acid in $CH_2Cl_2$-solution according to Tucker et al., "Nonsteroidal Antiandrogens. Synthesis and Structure-Activity Relationships of 3-Substituted Derivatives of 2-Hydroxypropionanilides," *J. Med. Chem.,* 31(5)954–959 (1988) gave R-8 with excellent yield (82%).

Scheme 2

Synthesis of (R)-isothiocyanate and Azide Analogs of Casodex

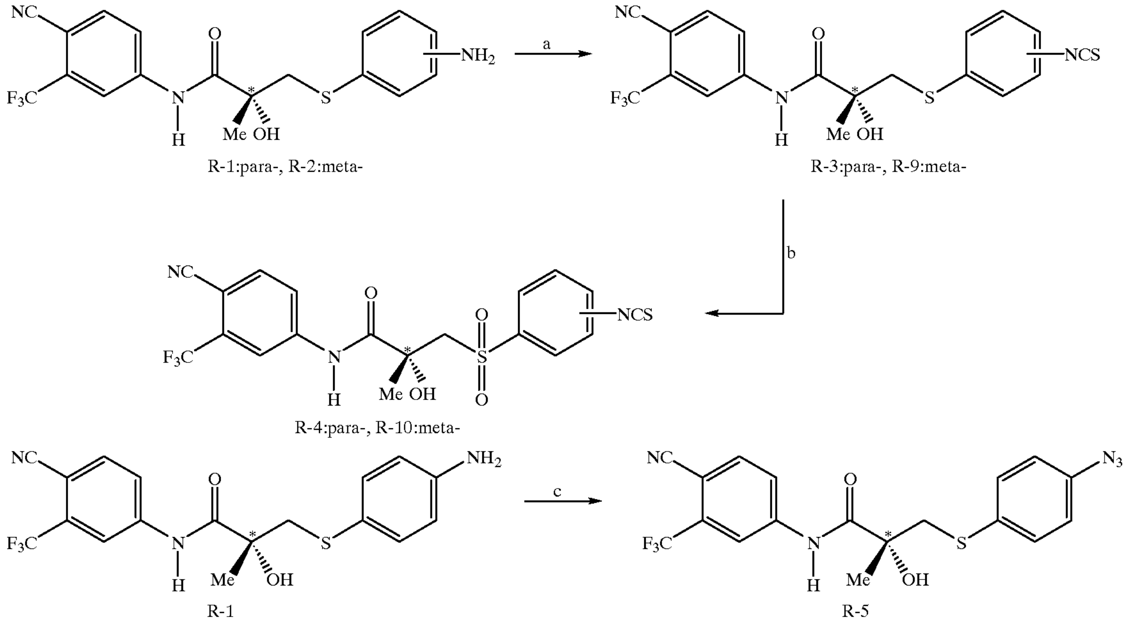

Scheme 3
Synthesis of (R)-Chloroacetamide and Bromoacetamide Analogs of Casodex

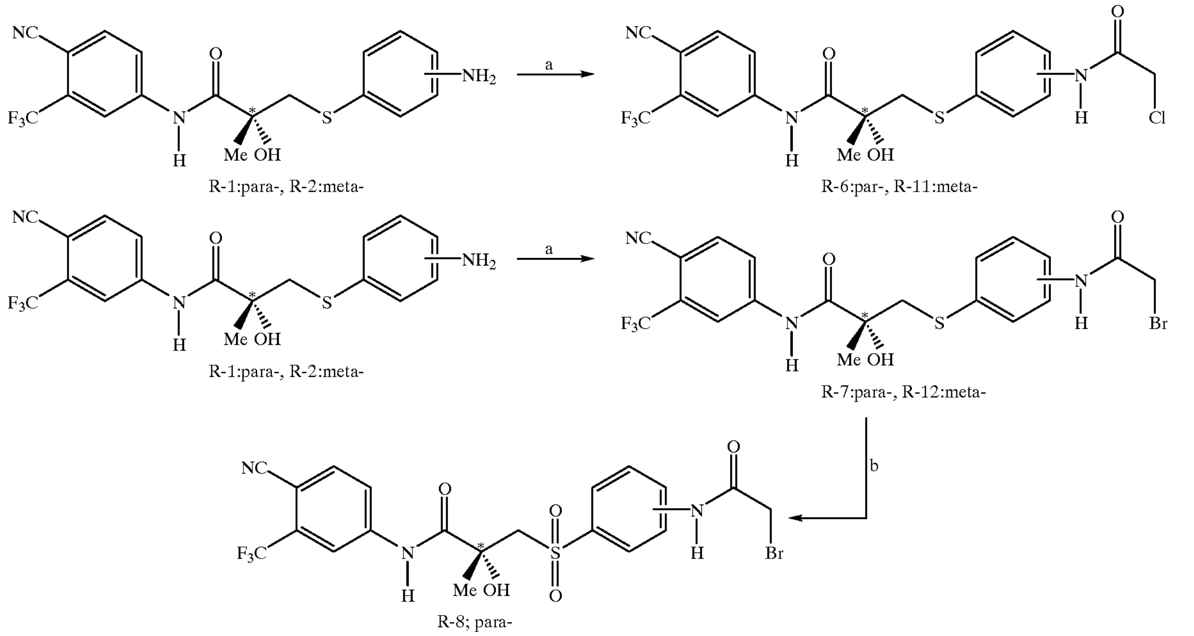

a) chloroacetyl chloride (or bromacetyl bromide), $iPr_2EtN$, $CH_2CH_2$, 0° C., 4h; b)m-chloroperbenzoic acid, $CH_2Cl_2$, 3h, R.T.

Example 2

Receptor binding studies for the compounds shown in Table 3 were conducted as follows.

Mibolerone (MIB) is a synthetic androgen with high affinity and high specificity for the AR.

Competitive displacement of $^3$H-MIB from AR binding sites by our compound was assessed as follows:

1. AR were isolated from rat ventral prostate tissue by differential centrifugation.

2. Samples of the following composition listed in Table 4 were incubated at 4° C. for 18 hours:

TABLE 4

| | |
|---|---|
| $^3$H-MIB | 1 nM |
| Triamcinolone | 1 $\mu$M |
| TRIS buffer | 10 mM |
| AR protein | 14.5 mg protein/ml, final concentration |
| Casodex analog | $10^{-6}$ $\mu$M to 10 $\mu$M |

Non-specific binding was determined by including MIB (1 $\mu$M) in the above incubate.

3. Bound $^3$H-MIB was separated by addition of a slurry of hydroxyapatite, and extracted from hydroxyapatite with ethanol.

4. Bound $^3$H-MIB was counted using liquid scintillation spectrometry.

Data Analysis

Percent Specific Binding=$(B/B_0)\times 100$

B =specific binding of $^3$H-MIB in the presence of a particular concentration of compound of interest $B_0$=specific binding of $^3$H-MIB in the absence of the compound Data were computer fitted to the equation:

$$\text{Specific Binding} = B_o\left(1 - \frac{C}{IC_{50} + C}\right)$$

C=isomer concentration $IC_{50}$=isomer concentration that reduces % specific binding by 50%.

Equilibrium dissociation constant of each isomer ($K_i$) was determined using the equation.

$$K_I = \frac{IC_{50} K_d}{L + K_d}$$

$K_d$=equil. dissociation constant of $^3$H-MIB

L=concentration of $^3$H-MIB

The results are shown in Table 3 above.

AR binding studies of the compounds listed in Table 3 showed that in all cases (R)-isomers had a higher AR binding affinity than (S)-isomers. This data is in agreement with the results found with Casodex enantiomers, Mukherjee et al., "Enantioselective Binding of Casodex to the Androgen Receptor," *Xenobiotica,* 22:117–22 (1996), ((R-isomers>>(S)-isomers).

Oxidation of thioester compounds to sulfoxide derivatives (R-3 to R-4, R-7 to R-8, R-9 to R-10) enhanced the binding ability of the compounds.

Comparison of the binding properties of the para- and the meta-substituted antiandrogens showed that substitution in the para-position gives better binding compounds. The most exciting example of this effect on substitution is compounds R-6 and R-11. Shifting the chloroacetamide substituent from the meta-to the para-position causes a dramatic (about three order of magnitude) increase in the $K_i$-value. Compounds R-4 and R-10, S-1 and S-2 show a less distinct effect. There is no difference in binding of compounds R-3 and R-9. However, compounds R-1 and R-2, S-3 and S-9 show the opposite dependence with the best binding ocuring with the meta-analog.

Variation of binding affinity in the series of para- and meta-substituted analogs is given below:

Para-substituted: Chloroacetamide R-6>azide R-5>amine R-1>bromoacetamide

R-7≈isothiocyanate R-3.

Meta-substituted: amine R-2>bromoacetamide R-12≈isothiocyanate R-9>chloroacetamide R-11.

Amino compounds bind to the AR better than bromoacetamides and isothiocyanates (R-1>R-7≈R-3, R-2>R-12≈R-9) which have fairly close $K_i$ values. The chloroacetamide analog has the highest binding in the para-position (R-6) and binds very poorly to the AR in the meta-position (R-11).

Compound R-6 was found to have the highest binding to the AR of any compounds.

Example 3

A series of electrophilic nonsteroidal compounds were designed and synthesized with the ability to irreversibly and permanently bind the AR, and thereby permanently inhibit the ability of testosterone ("T") and dihydrotestosterone ("DHT") to bind the androgen receptor. The ability of these compounds was evaluated to: (A) compete for binding to the AR, and (B) to irreversibly bind the AR and permanently inhibit binding by other agents. The experimental methods and results of these studies are summarized below.

A. Ability of Our Compounds to Complete for AR Binding

Methods

The ability of the compounds was evaluated to compete with mibolerone (MIB) for rat ventral prostate AR. MIB is a highly specific AR ligand which demonstrates greater affinity and specificity for the AR than DHT, is not metabolized like T and DHT, and is not light-sensitive as is the case for methyltrienolone (R1881), another commonly used AR radioligand. AR isolation was performed as follows. Bilateral orchiectomy was performed on male, Sprague-Dawley rats using sterile surgical procedures. Animals were allowed 24 hr for recovery and then were anesthetized a second time for tissue procurement. Ventral prostates were removed, weighed, and immediately immersed in an ice-cold solution of phosphate buffered saline. Ventral prostates were minced, homogenized, diluted in buffer, and then the tissue slurry was centrifuged at 105,000 g for 1 h at 0° C. The supernatant (cytosol) fraction containing the AR was decanted, stored at −80° C., and used as the AR source for binding studies. Our homogenization buffer consisted of 1.5 mM $Na_2EDTA$, 0.5 mM dithiothreitol, 0.25 M sucrose, 10 mM $Na_2MoO_4$, 1 mM phenylmethyl sulfonyl fluoride ("PMSF") in 10 mM TRIS, pH 7.4. Using this buffer, we isolated rat prostate AR and demonstrated that $^3$H-MIB binding in the preparation is comprised of about 90% specific binding to the AR and less than 10% to nonspecific binding sites. The first step was to determine the equilibrium dissociation constant ("$K_d$") of $^3$H-MIB in our AR preparation. Increasing concentrations of $^3$H-MIB ($10^{-11}$ to $10^{31\ 8}$ M) were incubated with AR at 4° C. for 18 hr, and then bound and unbound $^3$H-MIB separated using hydroxylapatite ("HAP"). Data were analyzed using a modified form of the Scatchard equation (i.e. $B/F=(-1/K_d)B+B_{max}/K_d$, where B is the concentration of radioligand ($^3$H-MIB) in the incubate present as ligand-AR complex, F is the concentration of free $^3$H-MIB present in the incubate, and $B_{max}$ is the maximum concentration of radioligand which can be bound in the incubate. A plot of (AR-bound $^3$H-MIB/free $^3$H-MIB) versus (AR-bound $^3$H-MIB) was constructed. The negative inverse of the slope of this plot yielded the value of $K_d$ for MIB, 0.182 nM, in the AR preparation. The relative binding affinity of each newly synthesized compound was then determined. Increasing concentrations ($10^{-12}$ to $10^{-5}$ M) of each compound were incubated with AR and a known concentration of $^3$H-MIB (1.0 nM). Data were plotted in terms of the specific binding (mean±S.D., n=3) expressed as a percent of control value (i.e., in the absence of competitor) on the ordinate versus the logarithm of the concentration of the competitor. The concentration of competitor required to inhibit specific binding by 50% ($IC_{50}$) was determined by computer-fitting the experimental data to the Hill equation (NLIN procedure, SAS, SAS Institute, Cary, N.C.). The $K_i$ for each compound was calculated by the following equation: $K_i=IC_{50}/(1+[L]/K_d)$, where $IC_{50}$ is the concentration of competitor which inhibits the binding of $^3$H-MIB by 50%, [L] is the concentration of $^3$H-MIB added (1.0 nM), and $K_d$ is the equilibrium dissociation constant for MIB (0.182 nM). The $K_i$ of the two endogenous compounds (i.e., T and DHT) were also determined.

Results

A number of affinity labeled ligands and precursors were synthesized, including S-nitro-thio-aniline ("S-NTA"), S-nitro-thio-isothiocyanate ("S-NT-NCS"), S-nitro-thio chloroacetamide ("S-NT-CAA"), and R- and S-Bromo-CyanoAnilide ("R-CAD" and "S-CAD", respectively). These analogs were selected for early synthesis to demonstrate that the organic chemistry with various affinity labels and precursors could be carried out. The chemical structures of these analogs and their AR binding affinities in rat prostate AR are shown in FIG. 1. AR binding affinities are reported in graphical form as log $K_i$ values. Smaller $K_i$ values indicate greater AR binding affinity. R-isomers are presented as solid bars in the FIGS. 1 and 2; S-isomers as dotted bars, and racemic mixtures as bars with diagonal lines.

Several previously synthesized compounds (i.e., Casodex and Thio-Casodex) are included for the sake of comparison. It is important to note that the AR binding affinities of the ligands (i.e., S-NTA, S-NT-NCS, and S-NT-CAA) are close to that of S-Casodex, demonstrating that the incorporation of these functional groups into the compound did not significantly interfere with AR binding ability. The $K_i$ value for T (1.09±0.2 nM, not pictured) was in agreement with values previously published by other investigators, indicating the validity of our results.

Synthesis was completed of several R-isomers of potential irrversible AR ligands, including four isothiocyanate ("NCS"), three bromoacetamide ("BAA"), and two chloroacetamide ("CAA") derivatives. Structures and $K_i$ values for these para(p) and meta (m)-substituted derivatives are presented in FIG. 2. In all cases, Casodex derivatives (sulfones, denoted as S in FIG. 2) showed greater binding affinities (i.e., lower $K_i$ values) than their corresponding un-oxidized thioprecursors (denoted as T in the figure): p-S-NCS>p-T-NCS, m-S-NCS>m T-NCS, and p-S-BAA>p-T-BAA. Of the isothiocyanate derivatives, the R-cyanotrifluoro sulfo-p-isothiocyanate derivative (p-S-NCS) bound with greatest affinity ($K_i$=31 nM). The remaining isothiocyanates and the acetamides (bromo and chloro), with one notable exception, demonstrated weaker interactions with the AR (i.e., $K_i$ values close to or considerably greater than 100 nM). The R-cyano-trifluoro-thio-p-chloroacetamide derivative (p-T-

CAA) bound the AR with extremely high affinity ($K_i$,3D=1.6 nM). These results demonstrate that we are able to develop a wide variety of potential irrversible compounds, and maintain binding affinities near the range of binding affinities of known antagonists for the AR. Thus, the aforementioned compounds (i.e., bromoacetamides, chloroacetamides, and isothiocyanates) were carried forward to studies to examine their irreversibility.

B. Ability of Our Compounds to Irreversibly Bind the AR

Methods

The proposed agents were designed to irreversibly bind the AR. The ability of the compounds to do so was examined using an AR exchange assay. Rat ventral prostate AR was prepared as previously described and used as the receptor source. AR was pre-incubated with reversible or potentially irreversible ligands (10 $\mu$M final concentration) in separate experiments at 4° C. for up to 12 hours. Control experiments with no ligand were performed to account for decreases in binding due to AR degradation. Hydroxylapatite ("HAP") was added to the ligand-cytosol mixture and allowed to incubate for an additional 15 min. The HAP-AR complex was centrifuged and then resuspended in ice cold homogenization buffer. This procedure was repeated twice to ensure complete removal of reversibly bound ligands. The HAP-AR complex was resuspended a final time in buffer containing 1 nM $^3$H-MIB. Separate tubes containing 5 $\mu$M unlabeled MIB were used in all experiments to determine the extent of non-specific binding. Incubations were maintained at 4° C. for an additional 12 hr, and then specifically AR-bound $^3$H-MIB determined as described above. Reversible ligands will dissociate from the AR during washing, and thus demonstrate near 100% recovery of exchangeable specific $^3$H-MIB binding sites as compared to controls. Irreversible AR binding by a ligand will appear as a significant decrease in exchangeable $^3$H-MIB binding sites. R-Casodex, a known reversible antiandrogen, and two reversible aniline derivatives synthesized in our laboratories (T-aniline and m-T-aniline) were included in the studies to demonstrate the validity of the experimental system.

Results

AR exchange assays were performed in order to assess the level of irreversible binding that was occurring with the compounds. The results are presented in FIG. 3. R-Casodex, R-CyanoTrifluoro-Thio-p-aniline ("p-T-aniline") and R-CyanoTrifluoro-Thio-m-aniline ("m-T-aniline") do not contain electrophilic groups and are, thus, incapable of irreversible binding to the AR.

As expected, exchangeable specific binding for these compounds (as a % of control) was near 100%. None of the bromoacetamide ("BAA") derivatives tested caused a decrease in exchangeable specific binding of $^3$H-MIB. However, the para-substituted isothiocyanate ("p-T NCS" and "p-S-NCS") and chloroacetamide ("p-T-CAA") derivatives significantly decreased exchangeable specific binding by $^3$H-MIB. The para-isothiocyanate derivatives of thio Casodex and Casodex ("p-T-NCS" and "p-S-NCS", respectively in the FIG. 3) decreased exchangeable binding to 16 and 15% of control, respectively. Likewise, the parachloroacetamide derivative of thio-Casodex ("p-T-CAA") decreased exchangeable specific binding to 25% of control values. These compounds, therefore, represent the first irreversibly binding compounds for the AR. With the exception of the meta-isothiocyanate derivative of Casodex ("m-S-NCS"), the meta-substituted derivatives of these same compounds showed no such ability for irreversible binding to the AR, suggesting that the para-substituted affinity ligands more favorably interact with a nucleophile in the ligand binding domain of the AR.

As a final point, it is important to note that the ability to irreversibly bind the AR was not directly related to the AR binding affinity. The p-isothiocyanate derivative of Thio-Casodex ("p-T-NCS") showed weaker binding affinity (i.e., $K_i$=390 nM), but was able to decrease exchangeable binding to the same extent as its corresponding sulfone derivative ("p-S-NCS", $K_i$=31 nM), supporting the contention that para-substituted isothiocyanate derivatives selectively seek out nucleophiles in the AR ligand binding domain. We also completed a preliminary experiment to examine time-dependent AR inactivation by the para-isothiocyanate derivative of Casodex ("p S-NCS", open circles) as compared to the reversible parent compound Casodex (closed circles) (FIG. 4). A lower concentration of the individual ligands (2 $\mu$M) was incubated for various periods of time before treatment with HAP, and subsequent exchange with 1 nM $^3$H-MIB. p-S NCS rapidly (i.e., within 0.5 hr) decreased the number of exchangeable AR binding sites to 50% of that observed in control incubations with no ligand. Exchangeable specific binding for Casodex was near 100% of control at all time points. In summary, these studies indicate that three of the compounds (i.e., p-T-NCS, p-S-NCS, and p-T-CAA) bind the AR irreversibly.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for treating prostate cancer in a patient comprising:

administering to the patient an effective amount of a compound having the formula:

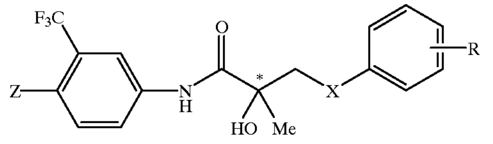

where

Z is NCS or CN,

R is $NH_2$, NCS, $N_3$ or $NHCOCH_2Y$,

X is S or $SO_2$, and

Y is a halogen or where

Z is NCS,

R is F, and

X is S or $SO_2$; and wherein the compound binds irreversibly to an androgen receptor of the patient.

2. The method according to claim 1, wherein Z is CN, X is S, and R is $NHCOCH_2Cl$.

3. The method according to claim 1, wherein Z is CN, X is S, and R is NCS.

4. The method according to claim 1, wherein Z is CN, X is $SO_2$, and R is NCS.

5. The method according to claim 1, wherein Z is NCS, X is $SO_2$, and R is F.

6. A compound having the formula:

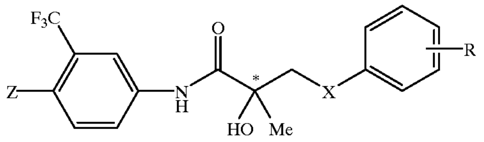

where
Z is NCS or CN,
R is $NH_2$, NCS, $N_3$ or $NHCOCH_2Y$,
X is S or $SO_2$, and
Y is a halogen or
where
Z is NCS,
R is F, and
X is S or $SO_2$; and
wherein the compound binds irreversibly to an androgen receptor of a mammal.

7. The compound according to claim 6, wherein Z is CN, X is S, and R is $NHCOCH_2Cl$.

8. The compound according to claim 6, wherein Z is CN, X is S, and R is NCS.

9. The compound according to claim 6, wherein Z is CN, X is $SO_2$, and R is NCS.

10. The compound according to claim 6, wherein Z is NCS, X is $SO_2$,and R is F.

11. A pharmaceutical composition comprising:
a pharmaceutically acceptable carrier and a compound having the formula

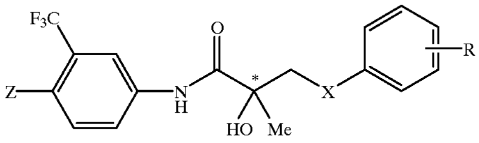

where
Z is NCS or CN,
R is $NH_2$, NCS, $N_3$ or $NHCOCH_2Y$,
X is S or $SO_2$, and
Y is a halogen or
where
Z is NCS,
R is F, and
X is S or $SO_2$.

12. The composition according to claim 11, wherein Z is CN, X is S, and R is $NHCOCH_2Cl$.

13. The composition according to claim 11, wherein Z is CN, X is S, and R is NCS.

14. The composition according to claim 11, wherein Z is CN, X is $SO_2$, and R is NCS.

15. The composition according to claim 11, wherein Z is NCS, X is $SO_2$, and R is F.

* * * * *